United States Patent [19]

Altman et al.

[11] Patent Number: 5,001,283

[45] Date of Patent: Mar. 19, 1991

[54] PROCESS FOR PREPARING AROMATIC ALKANOLS

[75] Inventors: Lawrence J. Altman, Cherry Hill; Philip J. Angevine; John P. McWilliams, both of Woodbury, all of N.J.

[73] Assignee: Mobil Oil Corp., Fairfax, Va.

[21] Appl. No.: 469,864

[22] Filed: Jan. 24, 1990

Related U.S. Application Data

[63] Continuation-in-part of Ser. No. 254,524, Oct. 6, 1988, Pat. No. 4,954,325, which is a continuation-in-part of Ser. No. 98,176, Sep. 18, 1987, abandoned, which is a continuation-in-part of Ser. No. 890,268, Jul. 29, 1986, abandoned.

[51] Int. Cl.$^5$ .............................................. C07C 33/18
[52] U.S. Cl. ..................................... 568/867; 568/715
[58] Field of Search ............................ 568/715, 867

[56] References Cited

U.S. PATENT DOCUMENTS

| | | | |
|---|---|---|---|
| 3,228,831 | 1/1968 | Nicholson et al. | 514/568 |
| 3,385,886 | 5/1968 | Nicholson et al. | 562/492 |
| 4,439,409 | 3/1984 | Puppe et al. | 423/328 |
| 4,443,643 | 4/1984 | Watson et al. | 585/437 |
| 4,507,512 | 3/1985 | Okumura et al. | 568/715 |
| 4,820,882 | 4/1989 | Eckhardt et al. | 568/715 |
| 4,826,667 | 5/1989 | Zones et al. | 423/328 |
| 4,849,401 | 7/1989 | Friedrich et al. | 568/715 |
| 4,943,667 | 7/1990 | Hoelderich et al. | 568/715 |

FOREIGN PATENT DOCUMENTS

| | | | |
|---|---|---|---|
| 0231860 | 8/1987 | European Pat. Off. | 502/64 |
| 0293032 | 11/1988 | European Pat. Off. | 502/64 |

Primary Examiner—Anthony McFarlane
Attorney, Agent, or Firm—Alexander J. McKillop; Charles J. Speciale; Dennis P. Santini

[57] ABSTRACT

Aromatic alkanols are provided by reacting an aromatic compound with a 1,2-alkylene oxide in the presence of a synthetic porous crystalline material possessing a Constraint Index of not greater than about 3. Thus, for example, isobutylbenzene is reacted with propylene oxide in the presence of zeolite Beta, ZSM-12 or MCM-22 to provide 2-(4-isobutylphenyl)propanol which can thereafter be oxidized to the corresponding carboxylic acid, the widely utilized anti-inflammatory agent ibuprofen (i.e., 2-(4-isobutylphenyl)-propionic acid).

18 Claims, No Drawings

PROCESS FOR PREPARING AROMATIC ALKANOLS

CROSS-REFERENCE TO RELATED APPLICATIONS

This application is a continuation-in-part of U.S. patent application Ser. No. 254,524, filed Oct. 6, 1988, and issued on Sept. 4, 1990 as U.S. Pat. No. 4,954,325 as a continuation-in-part of U.S. patent application Ser. No. 98,176, (now abandoned) filed Sept. 18, 1987, as a continuation-in-part of U.S. patent application Ser. No. 890,268, filed July 29, 1986.

BACKGROUND OF THE INVENTION

This invention relates to a process for preparing aromatic alkanols.

In the known process of preparing the commercially important aromatic alkanol 2-phenylethanol by reaction of the Grignard reagent, phenylmagnesium halide, with ethylene oxide, significant quantities of chlorohydrins and, some cases, initial rearrangement of the ethylene oxide to the aldehyde or ketone followed by reaction with the Grignard reagent, accompanies the desired reaction. Magnesium halide, $M_gX_2$, is thought to be responsible for most of these undesirable reactions.

U.S. Pat. Nos. 3,228,831 and 3,385,886 disclose compounds of the general formula

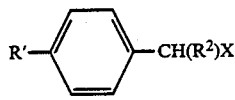

wherein R' represents alkyl ($C_3$–$C_4$), pentyl (except n-pentyl), alkylene ($C_2$–$C_4$), cycloalkyl ($C_5$–$C_7$) optionally substituted by a methyl group in the 1-position, alkoxy ($C_2$–$C_3$), alkylthio ($C_1$–$C_3$), allyloxy, phenoxy, phenylthio, cyclohexyloxy and cyclohexylthio when $R^2$ is hydrogen; or R' represents alkyl ($C_2$–$C_5$), branched alkyl ($C_6$–$C_7$), cycloalkyl ($C_3$–$C_7$) optionally substituted by a methyl group in the 1-position, alkoxy ($C_2$–$C_5$), alkylthio ($C_1$–$C_5$), alkenyloxy ($C_3$–$C_4$), alkenylthio ($C_3$–$C_5$), phenoxy, phenylthio, cycloalkyloxy ($C_3$–$C_7$), cycloalkylthio ($C_3$–$C_7$), alkylene ($C_2$–$C_4$) and halogen when $R^2$ is methyl; X represents $CH_2OH$, $COOR^3$ wherein $R^3$ represents hydrogen or alkyl ($C_1$–$C_4$) optionally substituted. These compounds, including the non-toxic inorganic and organic salts of the acids, i.e., those compounds wherein X is $COOR^3$ in which $R^3$ is hydrogen, are said to possess anti-inflammatory and/or analgesic and/or antipyretic properties. One particular compound within the foregoing general formula, ibuprofen (i.e., 2-(4-isobutylphenyl)propionic acid), which possesses the structure

is a widely utilized anti-inflammatory agent. Several methods are disclosed in these patents for the preparation of this and related propionic acids, i.e., hydrolysis of a nitrile intermediate, decarboxylation of a dicarboxylic acid intermediate, hydrolysis of an ester intermediate, dehydration of a hydroxy acid intermediate and simultaneous dehydration of a hydroxy nitrile with hydrolysis of the nitrile group to a carboxylic acid group. These patents also disclose the preparation of the alcohols

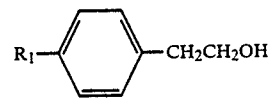

wherein $R^1$ is, inter alia, isobutyl, by reaction of the Grignard reagent $R_1PhMgCl$ with ethylene oxide. It is highly probable that this last-mentioned reaction is also accompanied by the same sort of undesirable side reactions as those discussed above in connection with the known synthesis of 2-phenylethanol employing a Grignard reagent.

SUMMARY OF THE INVENTION

In accordance with the present invention, an aromatic alkanol is prepared by the process which comprises reacting an aromatic compound with a 1,2-alkylene oxide in the presence of a synthetic porous crystalline material possessing a Constraint Index, as hereinafter defined, of less than about 3.

Unlike the known methods for preparing 2-phenylethanol and para-substituted phenylethanol discussed above which employ Grignard reagents, the process of this invention altogether avoids the use of Grignard reagents and thus avoids the problem of the competing side reactions which are associated with the use of Grignards.

DESCRIPTION OF SPECIFIC EMBODIMENTS

The entire contents of applications Ser. Nos. 254,524; 98,176; and 890,268 are incorporated herein by reference.

The aromatic compounds which can be reacted with 1,2-alkylene oxide to provide aromatic alkanol in accordance with this invention include mono- and polynuclear aromatic compounds possessing at least one hydrogen atom directly bonded to the aromatic nucleus and if substituted, possessing one or more ring substituents which do not significantly interfere with the reaction, (as would an electron withdrawing substituent such as nitro or nitrile). Acceptable ring substituents include such groups as hydrocarbyl, alkoxy, halogen, alkylthio, alkylamino, amido, and the like. The aromatic reactant can contain one or more hetero atoms provided such do not act as catalyst poisons under the reaction conditions selected. Specific aromatic compounds which are advantageously employed in the practice of this invention include benzene and alkyl-substituted benzenes such as toluene, ethylbenzene, the propylbenzenes, the butylbenzenes, and so forth.

Any of the known 1,2-alkylene oxides can be used in this process with ethylene oxide, propylene oxide and butylene oxide being preferred.

The process of this invention is especially useful for preparing the para-substituted phenyl alkanol 2-(4-isobutyl-phenyl) propanol by reacting isobutylbenzene with propylene oxide in the presence of the zeolite catalyst in accordance with the reaction

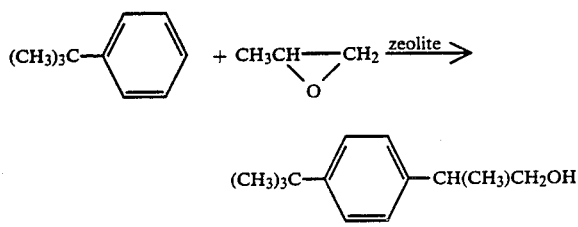

The product 2-(4-isobutylphenyl)propanol can thereafter be oxidized to the corresponding carboxylic acid in a known and conventional manner to provide ibuprofen in accordance with the reaction

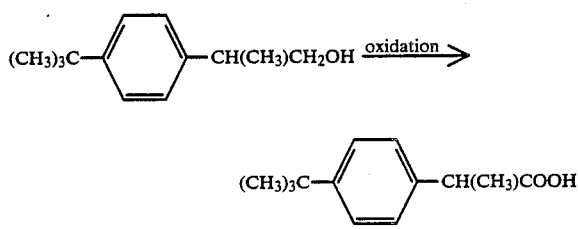

As mentioned above, the zeolite catalysts which are useful in the process of this invention are those possessing a Constraint Index of not greater than about 3 and preferably not greater than about 2.5.

The method by which Constraint Index is determined is described fully in U.S. Pat. No. 4,016,218, incorporated herein by reference for details of the method.

Constraint Index (CI) values for some typical zeolites including some which are suitable as catalysts in the process of this invention are:

|  | CI (at test temperature) |
|---|---|
| ZSM-4 | 0.5 (316° C.) |
| ZSM-5 | 6–8.3 (371° C.–316° C.) |
| ZSM-11 | 5–8.7 (371° C.–316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-48 | 3.5 (538° C.) |
| ZSM-50 | 2.1 (427° C.) |
| MCM-22 | 1.5 (454° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6–2.0 (316° C.–399° C.) |

The above-described Constraint Index is an important and even critical definition of those porous crystalline materials which are useful in the instant invention. The very nature of this parameter and the recited technique by which it is determined, however, admits of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g., temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites but that such are the cumulative result of several variables useful in the determination and calculation thereof. Thus, for a given zeolite exhibiting a CI valve within the range of 3 or less, depending on the temperature employed during the test method within the range of 290° C. to about 538° C., with accompanying conversion between 10% and 60%, the CI may vary within the indicated range of 3 or less. Accordingly, it will be understood to those skilled in the art that the CI as utilized herein, while affording a highly useful means for characterizing the zeolites of interest, is approximate taking into consideration the manner of its determination with the possibility in some instances of compounding variable extremes. However, in all instances, at a temperature within the above-specified range of 290° C. to about 538° C., the CI will have a value for any given zeolite of interest herein of not greater than about 3 and preferably not greater than about 2.5.

Some crystalline compositions which are especially useful in the process of this invention include Beta, MCM-22, ZSM-12 and PSH-3.

ZSM-12 is more particularly described in U.S. Pat. No. 3,832,449, the entire contents of which are incorporated by reference herein. The PSH-3 composition is described in U.S. Pat. No. 4,439,409, the entire contents of which are incorporated by reference herein. Zeolite Beta is described in U.S. Pat. No. 3,308,069, the entire contents of which are incorporated by reference herein.

Zeolite MCM-22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

wherein R is an organic component. The Na and R components are associated with the zeolite as a result of their presence during crystallization, and are easily removed by post-crystallization methods hereinafter more particularly described.

Zeolite MCM-22 is thermally stable and exhibits high surface area (greater than 400 m²/gm as measured by the BET (Bruenauer, Emmet and Teller test) and unusually large sorption capacity when compared to previously described crystal structures having similar X-ray diffraction patterns. As is evident from the above formula, MCM-22 is synthesized nearly free of Na cations. It and the other useful zeolite can be used as catalysts with acid activity without an exchange step. To the extent desired, however, the original sodium cations of the as-synthesized zeolite catalysts can be replaced in accordance with techniques well known in the art, at least in part, by ion exchange with other cations. Preferred replacing cations include metal ions, hydrogen ions, hydrogen precursor, e.g., ammonium, ions and mixtures thereof. Particularly preferred cations are those which tailor the catalytic activity for transalkylation/disproportionation. These include hydrogen, rare earth metals and metals of Groups IIA, IIIA, IVA, IB, IIB, IIIB, IVB and VIII of the Periodic Table of the Elements.

In its calcined form, zeolite MCM-22 appears to be made up of a single crystal phase with little or no detectable impurity crystal phases and has an X-ray diffraction pattern including the lines listed in Table I below:

TABLE I

| Interplanar d-Spacing (A) | Relative Intensity, I/Io × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an X-ray diffraction pattern including the following lines:

TABLE II

| Interplanar d-Spacing (A) | Relative Intensity, I/Io × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 I/I$_o$, where I$_o$ is the intensity of the strongest line or peak, and d (obs.) the interplanar spacing in Angstroms Units (A), corresponding to the recorded lines, were determined. In Tables I and II, the relative intensities are given in terms of the symbols W=weak, M=medium, S=strong and VS=very strong. In terms of intensities, these may be generally designated as follows:

W=0-20
M=20-40
S=40-60
VS=60-100

It should be understood that these X-ray diffraction patterns are characteristic of all species of zeolite MCM-22. The sodium form as well as other cationic forms of this zeolite reveal substantially the same pattern with some minor shifts in interplanar spacing and variation in relative intensity. Other minor variations can occur depending on the Y to X, e.g., silicon to aluminum, mole ratio of the particular sample, as well as its degree of thermal treatment.

Zeolite MCM-22 can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
|---|---|---|
| YO$_2$/X$_2$O$_3$ | 10–60 | 10–40 |
| H$_2$O/YO$_2$ | 5–100 | 10–50 |
| OH$^-$/YO$_2$ | 0.01–1.0 | 0.1–0.5 |
| M/YO$_2$ | 0.01–2.0 | 0.1–1.0 |
| R/YO$_2$ | 0.05–1.0 | 0.1–0.5 |

In a preferred method of synthesizing zeolite MCM-22, the YO$_2$ reactant contains a substantial amount of solid YO$_2$, e.g., at least about 30 wt. % solid YO$_2$. Where YO$_2$ is silica, the use of a silica source containing at least about 30 wt. % solid silica, e.g., Ultrasil (a precipitated, spray dried silica containing about 90 wt. % silica) or HiSil (a precipitated hydrated SiO$_2$ containing about 87 wt. % silica, about 6 wt. % free H$_2$O and about 4.5 wt. % bound H$_2$O of hydration and having a particle size of about 0.02 micron) favors MCM-22 crystal formation from the above mixture. If another source of oxide of silicon, e.g., Q-Brand (a sodium silicate comprised of about 28.8 wt. % of SiO$_2$, 8.9 wt. % Na$_2$O and 62.3 wt. % H$_2$O) is used, crystallization may yield little if any MCM-22 crystalline material and impurity phases of other crystal structures, e.g., ZSM-12, may be produced. Preferably, therefore, the YO$_2$, e.g., silica, source contains at least about 30 wt. % solid YO$_2$, e.g., silica, and more preferably at least about 40 wt. % solid YO$_2$, e.g., silica.

Crystallization of the MCM-22 crystalline material can be carried out at either static or stirred conditions in a suitable reactor vessel such as, e.g., polypropylene jars or teflon lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals (based on total weight) of the crystalline product.

The zeolite conversion catalysts herein can be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be introduced in the catalyst composition by way of co-crystallization, exchanged into the composition to the extent a Group IIIA element, e.g., aluminum, is in the structure, impregnated therein or intimately physically admixed therewith. Such component can be impregnated in, or on, the zeolite such as, for example, by, in the case of platinum, treating the zeolite with a solution containing a platinum metal-containing ion. Thus, suitable platinum compounds for this purpose include chloroplatinic acid, platinous chloride and various compounds containing the platinum amine complex.

The zeolite catalysts, especially in their metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to their use in the process of this invention, the zeolite crystals should be dehydrated, at least partially. This can be done by heating the crystals to a temperature in the range of from about 200° C. to about 595° C. in an inert atmosphere, such as air, nitrogen, etc. and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

The zeolite catalysts employed herein can be shaped into a wide variety of particle sizes. Generally speaking, the particles can be in the form of a powder, a granule, or a molded product such as an extrudate having a particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

It may be desired to incorporate the selected zeolite catalyst with another material which is resistant to the temperatures and other conditions employed in the process of this invention. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the catalyst zeolite, i.e., combined therewith or present during its synthesis, which itself is catalytically active may change the conversion and/or selectivity of the catalyst. Inactive materials suitably serve as diluents to control the amount of conversion so that aromatic alkanol products can be obtained economically and orderly without employing other means for controlling the rate of reaction. These materials may be incorporated into naturally occurring clays, e.g., bentonite and kaolin, to improve the crush strength of the catalyst under commercial alkylation operating conditions. Said materials, i.e., clays, oxides, etc., function as binders for the catalyst. It is desirable to provide a catalyst having good crush strength because in commercial use, it is desirable to prevent the catalyst from breaking down into powder-like materials. These clay binders have been employed normally only for the purpose of improving the crush strength of the catalyst.

Naturally occurring clays which can be composited with the zeolite catalyst herein include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with zeolite also include inorganic oxides, notably alumina.

In addition to the foregoing materials, the zeolite catalyst can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia. It may also be advantageous to provide at least a part of the foregoing matrix materials in colloidal form so as to facilitate extrusion of the bound catalyst component(s).

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

The stability of the zeolite catalyst may be increased by steaming, with suitable steam stabilization conditions including contacting the catalyst with, for example, 5-100% steam at a temperature of at least about 300° C. (e.g. 300°-650° C.) for at least one hour (e.g. 1-200 hours) at a pressure of 100-2,500 kPa. In a more particular embodiment, the catalyst can be made to undergo steaming with 75-100% steam at 315°-500° C. and atmospheric pressure for 2-25 hours.

The process of this invention is conducted such that the organic reactants, i.e., the aromatic compound and the 1,2-alkylene oxide, are brought into contact with the zeolite MCM-22 catalyst composition in a suitable reaction zone such as, for example, in a flow reactor containing a fixed bed of the catalyst composition, under effective reaction conditions. In general, such conditions include a temperature of from about 0° C. to about 500° C., a pressure of from about 0.2 to about 250 atmospheres, a feed weight hourly space velocity (WHSV) of from about 0.1 to about 500 and an aromatic compound to 1,2-alkylene oxide mole ratio of from about 0.1:1 to about 50:1. The WHSV is based upon the weight of the catalyst composition employed, i.e., the total weight of active catalyst (and binder if present). Preferred reaction conditions include a temperature within the approximate range of from about 100° C. to about 350° C., a pressure of from about 1 to about 25 atmospheres, a WHSV of from about 0.5 to about 100 and an aromatic compound to 1,2-alkylene oxide mole ratio of from about 0.5:1 to about 10:1. The reactants can be in either the vapor phase or the liquid phase and can be neat, i.e., free from intentional admixture or dilution with other material, or they can be brought into contact with the zeolite catalyst composition with the aid of carrier gases or diluents such as, for example, hydrogen or nitrogen.

The process described herein can be carried out as a batch-type, semi-continuous or continuous operation utilizing a fixed or moving bed catalyst system. A preferred embodiments entails use of a catalyst zone wherein the hydrocarbon charge is passed concurrently or countercurrently through a moving bed of particle-form catalyst. The latter, after use, is conducted to regeneration zone where coke is burned from the catalyst in an oxygen-containing atmosphere (such as air) at elevated temperature, after which the regenerated catalyst is recycled to the conversion zone for further contact with the organic reactants.

In order to more fully illustrate the process of this invention and the manner of practicing same, the following examples are presented. In Examples 1 to 14 which are illustrative of the synthesis of zeolite MCM-22, whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or or 40 Torr cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the MCM-22 crystalline material, the decrease in pressure caused the manostat to open a valve which admitted more adsorbate vapor to the chamber to restore the above control pressures. Sorption was complete when the pressure change was not sufficient to activate the manostate. The increase in weight was calculated as the adsorption capacity of the sample in g/100 g of calcined adsorbent. Zeolite MCM-22 always exhibits Equilibrium Adsorption values of greater than about 10 wt. % for water vapor, greater than about 4.5 wt. %, usually greater than about 7 wt. % for cyclohexane vapor and greater than about 10 wt. % for n-hexane vapor. These vapor sorption capacities are a notable distinguishing feature of zeolite MCM-22.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of a highly active silica-alumina cracking catalyst taken as an Alpha of 1 (Rate Constant=0.016 sec$^{-1}$). The Alpha Test is described in U.S. Pat. No. 3,354,078, in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

EXAMPLE 1

One part of sodium aluminate (43.5% $Al_2O_3$, 32.2% $Na_2O$, 25.6% $H_2O$), was dissolved in a solution containing one part of 50% NaOH solution and 103.13 parts $H_2O$. To this was added 4.50 parts hexamethyleneimine. The resulting solution was added to 8.55 parts of Ultrasil, a precipitated, spray-dried silica (about 90% $SiO_2$).

The reaction mixture had the following composition, in mole ratios:

| | |
|---|---|
| $SiO_2/Al_2O_3$ = | 30.0 |
| $OH^-/SiO_2$ = | 0.18 |
| $H_2O/SiO_2$ = | 44.9 |
| $Na/SiO_2$ = | 0.18 |
| $R/SiO_2$ = | 0.35 | where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table III. The sorption capacities of the calcined material were measured to be:

| | |
|---|---|
| $H_2O$ (12 Torr) | 15.2 wt. % |
| Cyclohexane (40 Torr) | 14.6 wt. % |
| n-Hexane (40 Torr) | 16.7 wt. % |

The surface area of the calcined crystalline material was measured to be 494 m$^2$/g.

The chemical composition of the uncalcined material was determined to be as follows:

| Component | wt. % |
|---|---|
| $SiO_2$ | 66.9 |
| $Al_2O_3$ | 5.40 |
| Na | 0.03 |
| N | 2.27 |
| Ash | 76.3 |
| $SiO_2/Al_2O_3$, mole ratio = | 21.1 |

TABLE III

| Degrees 2-Theta | Interplanar d-Spacing (A) | I/I$_o$ |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |

TABLE III-continued

| Degrees 2-Theta | Interplanar d-Spacing (A) | I/I$_o$ |
|---|---|---|
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLES 3–5

Three separate synthesis reaction mixtures were prepared with compositions indicated in Table IV. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days, respectively, in a stainless steel, stirred (350 rpm) autoclave at autogenous pressure. Solids were separated from any unreacted components by filtration and then water washed, followed by drying at 120° C. The product crystals were analyzed by X-ray diffraction. Sorption, surface area and chemical analyses results are presented in Table IV. The sorption and surface area measurements were of the calcined product.

TABLE IV

| Example | 3 | 4 | 5 |
|---|---|---|---|
| Synthesis Mixture, mole ratios | | | |
| SiO$_2$/Al$_2$O$_3$ | 30.0 | 30.0 | 30.0 |
| OH$^-$/SiO$_2$ | 0.18 | 0.18 | 0.18 |
| H$_2$O/SiO$_2$ | 19.4 | 19.4 | 44.9 |
| Na/SiO$_2$ | 0.18 | 0.18 | 0.18 |
| R/SiO$_2$ | 0.35 | 0.35 | 0.35 |
| Product Composition, Wt. % | | | |
| SiO$_2$ | 64.3 | 68.5 | 74.5 |
| Al$_2$O$_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| SiO$_2$/Al$_2$O$_3$, mole ratio | 22.5 | 20.9 | 26.0 |
| Adsorption, Wt. % | | | |
| H$_2$O | 14.9 | 13.6 | 14.6 |
| Cyclohexane | 12.5 | 12.2 | 13.6 |
| n-Hexane | 14.6 | 16.2 | 19.0 |
| Surface Area, n$^2$/g | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a further preparation of the present zeolite, 4.49 parts of hexamethyleneimine was added to a solution containing 1 part of sodium aluminate, 1 part of 50% NaOH solution and 44.19 parts of H$_2$O. To the combined solution was added 8.54 parts of Ultrasil silica. The mixture was crystallized with agitation at 145° C. for 59 hours and the resultant product was water washed and dried at 120° C.

Product chemical composition, surface area and adsorption analyses results are as set forth in Table V:

TABLE V

| Product Composition uncalcined | 12.1 wt. % |
|---|---|
| C | 12.1 wt. % |
| N | 1.98 wt. % |
| Na | 640 ppm |
| Al$_2$O$_3$ | 5.0 wt. % |
| SiO$_2$ | 74.9 wt. % |
| SiO$_2$/Al$_2$O$_3$, mole ratio | 25.4 |
| Adsorption, wt. % | |
| Cyclohexane | 9.1 |
| n-Hexane | 14.9 |
| H$_2$O | 16.8 |
| Surface Area, m$^2$/g | 479 |

EXAMPLE 8

Twenty-five grams of solid crystal product from Example 7 were calcined in a flowing nitrogen atmosphere at 538° C. for 5 hours, followed by purging with 5% oxygen gas (balance N$_2$) for another 16 hours at 538° C.

Individual 3 g samples of the calcined material were ion-exchanged with 100 ml of 0.1N TEABr, TPABr and LaCl$_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| Exchange Ions Ionic Composition, wt. % | TEA | TPA | La |
|---|---|---|---|
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite MCM-22 has very good stability under severe hydrothermal treatment.

EXAMPLE 11

This example illustrates the preparation of the present zeolite where X in the general formula, supra, is boron.

Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:

| | |
|---|---|
| $SiO_2/B_2O_3 =$ | 6.1 |
| $OH^-/SiO_2 =$ | 0.06 |
| $H_2O/SiO_2 =$ | 19.0 |
| $K/SiO_2 =$ | 0.06 |
| $R/SiO_2 =$ | 0.30 | where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 540° C. and found to have the following sorption capacities:

| | |
|---|---|
| $H_2O$ (12 Torr) | 11.7 wt. % |
| Cyclohexane (40 Torr) | 7.5 wt. % |
| n-Hexane (40 Torr) | 11.4 wt. % |

The surface area of the calcined crystalline material was measured (BET) to be 405 $m^2/g$.

The chemical composition of the uncalcined material was determined to be as follows:

| | |
|---|---|
| N | 1.94 wt. % |
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio = | 1406 |
| $SiO_2/(Al + B)_2O_3$, molar ratio = | 25.8 |

EXAMPLE 12

A portion of the calcined crystalline product of Example 11 was treated with $NH_4Cl$ and again calcined. The final crystalline product was tested in the Alpha Test and found to have an Alpha Value of 1.

EXAMPLE 13

This example illustrates another preparation of the zeolite in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:

| | |
|---|---|
| $SiO_2/B_2O_3 =$ | 12.3 |
| $OH^-/SiO_2$ 32 | 0.056 |
| $H_2O/SiO_2 =$ | 18.6 |
| $K/SiO_2 =$ | 0.056 |
| $R/SiO_2 =$ | 0.30 | where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

| | |
|---|---|
| $H_2O$ (12 Torr) | 14.4 wt. % |
| Cyclohexane (40 Torr) | 4.6 wt. % |
| n-Hexane (40 Torr) | 14.0 wt. % |

The surface area of the calcined crystalline material was measured to be 438 $m^2/g$.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio = | 249 |
| $SiO_2/(Al + B)_2O_3$, molar ratio = | 28.2 |

EXAMPLE 14

A portion of the calcined crystalline product of Example 13 was tested in the Alpha Test and found to have an Alpha Value of 5.

EXAMPLE 15

This example illustrates three separate preparations of 2-(4-isobutylphenyl)propanol, an intermediate in the synthesis of ibuprofen, in accordance with the process of this invention.

Isobutylbenzene (268 g; 2 moles) and propylene oxide (29 g; 0.5 mole) are introduced into three separate 1 liter autoclaves loaded with 20 g of catalyst. The first autoclave has catalyst comprising 65 wt. % MCM-22 prepared as above and 35 wt. % alumina binder. The catalyst of the second autoclave is 65 wt. % zeolite Beta prepared as in U.S. Pat. No. 3,308,069 and 35 wt. % alumina binder. The catalyst of the third autoclave is 65 wt. % ZSM-12 prepared as in U.S. Pat. No. 3,382,449 and 35 wt. % alumina binder. Reaction conditions are 150° C. and 400 psig. After a reaction time of 1 hour, the reaction products from each autoclave contain 2-(4-isobutylphenyl)propanol.

Following its recovery from unreacted isobutylbenzene in each instance, the 2-(4-isobutylphenyl)propanol reaction products are oxidized with chromic acid to provide ibuprofen.

What is claimed is:

1. A process for preparing an aromatic alkanol which comprises reacting an aromatic compound with a 1,2-alkylene oxide in the presence of catalyst comprising a synthetic porous crystalline material possessing a Constraint Index of not greater than about 3, wherein the crystalline material is characterized by an x-ray diffraction pattern including values substantially as set forth in Table I of the specification.

2. The process of claim 1 wherein the crystalline material possesses a Constraint Index of not greater than about 2.5.

3. The process of claim 1 wherein the crystalline material is characterized by an x-ray diffraction pattern including values substantially as set forth in Table II of the specification.

4. The process claim 1 wherein the crystalline material has a composition comprising the molar relationship $$X_2O_3:(n)YO_2,$$

wherein n is at least about 10, X is a trivalent element and Y is a tetravalent element.

5. The process of claim 1 wherein the crystalline material possesses equilibrium adsorption capacities of greater than about 4.5 wt. % for cyclohexane vapor and greater than about 10 wt. % for n-hexane vapor.

6. The process of claim 4 wherein X is selected from the group consisting of aluminum, boron, gallium and combinations thereof and Y is selected from the group consisting of silicon, germanium and combinations thereof.

7. The process of claim 4 wherein X comprises aluminum and Y comprises silicon.

8. The process of claim 1 wherein the crystalline material has been treated to replace original cations, at least in part, with a cation or mixture of cations selected from the group consisting of hydrogen, hydrogen precursors, rare earth metals, and metals of Groups IIA, IIIA, IVA, IB, IIB, IIIB, IVB, VIB and VIII of the Periodic Table.

9. The process of claim 1 wherein the crystalline material has been thermally treated at a temperature up to about 925° C. in the presence or absence of steam.

10. The process of claim 1 wherein the aromatic compound is maintained in a molar excess relative to the 1,2-alkylene oxide.

11. The process of claim 1 wherein the aromatic compound is maintained in a 2 to 5 mole excess relative to the 1,2-alkylene oxide compound.

12. The process of claim 1 wherein the aromatic compound is benzene or an alkyl-substituted benzene.

13. The process of claim 1 wherein the 1,2-alkylene oxide is ethylene oxide, propylene oxide or butylene oxide.

14. The process of claim 1 wherein the aromatic compound is benzene and the 1,2-alkylene oxide is ethylene oxide.

15. The process of claim 1 wherein the aromatic compound is isobutylbenzene, the 1,2-alkylene oxide is propylene oxide, and the aromatic alkanol is 2-(4-isobutylphenyl)propanol.

16. The process of claim 1 wherein the reaction conditions include a temperature of from about 0° C. to about 500° C., a pressure of from about 0.2 to about 250 atmospheres, a feed weight hourly space velocity of from about 0.1 to about 500 hr$^{-1}$ and an aromatic compound to 1,2-alkylene oxide mole ratio of from about 0.1:1 to about 50:1.

17. The process of claim 1 wherein said synethic porous crystalline mater composited with a matrix material.

18. The process of claim 17 wherein said matrix material comprises an oxide selected from the group consisting of silica, alumina, zirconia, titania, beryllia, magnesia, thoria, and combinations thereof.

* * * * *

UNITED STATES PATENT AND TRADEMARK OFFICE
CERTIFICATE OF CORRECTION

PATENT NO. : 5,001,283

DATED : March 19, 1991

INVENTOR(S) : L.J. Altman et al.

It is certified that error appears in the above-identified patent and that said Letters Patent is hereby corrected as shown below:

Col. 4, line 12, "valve" should be --value--

Col. 6, line 35, "$CH^-$" should be --$OH^-$--

Col. 12, line 15, delete "12.1 wt.%"

Col. 13, line 61, "$OH^-/SiO_2^{32}$" should be --$OH^-/SiO_2$--

Col. 16, claim 17, should read, --The process of Claim 1 wherein said synthetic porous crystalline material is composited with a matrix material.--

Signed and Sealed this

Twenty-fifth Day of August, 1992

*Attest:*

DOUGLAS B. COMER

*Attesting Officer*   *Acting Commissioner of Patents and Trademarks*